US006242486B1

(12) United States Patent
Thornton et al.

(10) Patent No.: US 6,242,486 B1
(45) Date of Patent: Jun. 5, 2001

(54) LONG CHAIN CARBOXYBETAINES IN ANTIMICROBIAL FORMULATIONS

(75) Inventors: Charles G. Thornton, Gaithersburg, MD (US); Kevin A. Nash, Glendale, CA (US)

(73) Assignee: Integrated Research Technology, LLC, Baltimore, MD (US)

( * ) Notice: Subject to any disclaimer, the term of this patent is extended or adjusted under 35 U.S.C. 154(b) by 0 days.

(21) Appl. No.: 09/284,250

(22) PCT Filed: Oct. 10, 1997

(86) PCT No.: PCT/US97/18256

§ 371 Date: Apr. 9, 1999

§ 102(e) Date: Apr. 9, 1999

(87) PCT Pub. No.: WO98/16234

PCT Pub. Date: Apr. 23, 1998

Related U.S. Application Data

(63) Continuation of application No. 08/730,733, filed on Oct. 11, 1996, now abandoned.

(51) Int. Cl.[7] .................................................. A01N 37/30

(52) U.S. Cl. ............................................................ 514/556

(58) Field of Search ............................................ 514/556

(56) References Cited

U.S. PATENT DOCUMENTS

| 4,062,976 | 12/1977 | Michaels | 424/319 |
|---|---|---|---|
| 4,075,350 | 2/1978 | Michaels | 424/316 |
| 4,107,328 | 8/1978 | Michaels | 424/316 |
| 4,145,436 | 3/1979 | Michaels | 424/273 |
| 4,183,952 | 1/1980 | Michaels | 424/316 |
| 4,839,158 | 6/1989 | Michaels | 424/54 |
| 5,244,652 | 9/1993 | Michaels | 424/54 |
| 5,389,676 | 2/1995 | Michaels | 514/556 |
| 5,403,864 | 4/1995 | Bruch et al. | 514/721 |
| 5,439,681 | 8/1995 | Khan et al. | 424/400 |

FOREIGN PATENT DOCUMENTS

| 202 494 | 6/1983 | (CS) . |
|---|---|---|
| 56-25139 | 3/1981 | (JP) . |
| 4-134025 | 5/1992 | (JP) . |
| WO 95/27076 | 10/1995 | (WO) . |

OTHER PUBLICATIONS

Patent Abstracts of Japan, English language abstract for JP 9–157700, published Jun. 17, 1997.
Patent Abstracts of Japan, English language abstract for JP 9–235369, published Sep. 9, 1997.
Cella, J.A. et al., "The Relation of Structure and Critical Concentration to the Bactericidal Activity of Quaternary Ammonium Salts," *J. Am. Chem. Soc.* 74:2061–2062 (1952).

Chapin, K., "Chapter 4: Clinical Microscopy," in *Manual of Clinical Microbiology*, 6th ed., Murray, P.R. et al., eds., ASM Press, Washington, DC, pp. 33–51 (Mar., 1995).
Hancock, R.E.W., "Alterations in Outer Membrane Permeability," *Ann. Rev. Microbiol.* 38:237–264 (1984).
Isenberg, H.D. and R.F. D'Amoto, "Chapter 2: Indigenous and Pathogenic Microorganisms of Humans," in *Manual of Clinical Microbiology*, 6th ed., Murray, P.R. et al., eds., ASM Press, Washington, DC, pp. 5–18 (1995).
Joklik, W.K. et al., "Chapter 1: The Historical Development of Medical Microbiology," in *Zinsser Microbiology*, 20th ed., Appleton & Lange, Norwalk, CT, pp. 3–7 (1992).
Joklik, W.K. et al., "Chapter 2: The Classification and Identification of Bacteria," in *Zinsser Microbiology*, 20th ed., Appleton & Lange, Norwalk, CT, pp. 8–17 (1992).
Joklik, W.K. et al., "Chapter 6: Composition, Structure, and Biosynthesis of Bacterial Cell Envelope and Energy Storage Polymers," in *Zinsser Microbiology*, 20th ed., Appleton & Lange, Norwalk, CT, pp. 76–93 (1992).
Kent, P.T. et al., "Public Health Mycobacteriology," in *A Guide for the Level III Laboratory*, U.S. Department of Health and Human Services, Centers for Disease Control, pp. 31–46 (1985).
Knapp, C. et al., "5.16. Tests To Assess Bactericidal Activity," in *Clinical Microbiology Procedures Handbook*, vol. I, Isenberg, H.D., ed., American Society for Microbiology, Washington, DC, pp. 5.16.1–5.16.33 (1992).
Kubica, G.P. et al., "Sputum Digestion and Decontamination with N–Acetyl–L–Cysteine–Sodium Hydroxide for Culture of Mycobacteria," *Am. Rev. Resp. Dis.* 87:775–779 (1963).
Loulergue, J. et al., "Changes in microbial ecology and use of cloxacillin," *J. Hosp. Infect.* 27:275–283 (Aug., 1994).
Martin, M.A., "Nosocomial Infections in Intensive Care Units: An Overview of Their Epidemiology, Outcome, and Prevention," *New Horizons* 1:162–171 (May, 1993).
Nikaido, H. and M. Vaara, "Molecular Basis of Bacterial Outer Membrane Permeability," *Microbiol. Rev.* 49:1–32 (Mar., 1985).
Nilsson, P.–G. et al., "The Upper Consolute Boundary in Zwitterionic Surfactant–Water Systems," *J. Phys. Chem.* 88:6357–6362 (1984).
Pittet, D. and R.P. Wenzel, "Nosocomial Bloodstream Infections. Secular Trends in Rates, Mortality, and Contribution to Total Hospital Deaths," *Arch. Intern. Med.* 155:1177–1184 (Jun., 1995).

(List continued on next page.)

Primary Examiner—Kevin E. Weddington
(74) Attorney, Agent, or Firm—Sterne, Kessler, Goldstein & Fox P.L.L.C.

(57) ABSTRACT

Compositions containing long chain carboxybetaines, and their use in antimicrobial formulations, are described. The compositions and methods are especially useful against gram positive microorganisms such as *Staphylococcus* and gram negative microorganisms such as *Escherichia, Salmonella* and *Pseudomonas*.

23 Claims, 4 Drawing Sheets

OTHER PUBLICATIONS

Ruoff, K.L., "Chapter 25: Leuconostoc, Pediococcus, Stomatococcus, and Miscellaneous Gram–Positive Cocci That Grow Aerobically," in *Manual of Clinical Microbiology*, 6th ed., Murray, P.R. et al., eds., ASM Press, Washington, DC, pp. 315–323 (1995).

Siddiqi, S.H. et al., "A New Antimicrobial Mixture (PANTA) for Effective Suppression of Non–Mycobacterial Contamination During Primary Isolation of Mycobacteria," *American Society of Microbiology Annual Meeting*, Washington, DC, Abstract No. U–35, p. 125 (1986).

Tartar, H.V. and K.A. Wright, "Studies of Sulfonates. III. Solubilities, Micelle Formation and Hydrates of the Sodium Salts of the Higher Alkyl Sulfonates," *J. Am. Chem. Soc.* 61:539–544 (1939).

Tartar, H.V. and R.D. Cadle, "Studies of Sulfonates. VI. The Effect of Sodium Chloride on the Solubility of Sodium Dodecylsulfonate and Sodium Tetradecylsulfonate. The Solubility at 50°C. of Calcium Dodecylsulfonate and Calcium Dodecyl Sulfate in Aqueous Solutions of the Corresponding Sodium Salts," *J. Phys. Chem.* 43:1173–1179 (1939).

Tsubone, K. and N. Uchida, "Syntheses of 2–(N–2–Hydroxyalkyl–N,N–Dimethylammonio) Ethyl Hydrogen Phosphates and Their Physicochemical and Antimicrobial Properties," *J. Am. Oil Chem. Soc.* 67:394–399 (Jun., 1990).

Tsubone, K. et al., "Relation between Structure and Antimicrobial Activity of 2–(N,N,N–Trialkylammonio)alkyl Hydrogen Phosphates," *J. Pharmaceut. Sci.* 80:441–444 (May, 1991).

Tsujii, K. and J. Mino, "Krafft Point Depression of Some Zwitterionic Surfactants by Inorganic Salts," *J. Phys. Chem.* 82:1610–1614 (1978).

Tsujii, K. and T. Takeuchi, "Krafft Point Depression of Some Zwitter Ionic Surfactants by Inorganic salts. II.," *Yakagaku* 30:495–499 (1981).

Vermaat, J.H. et al., "An epidemiologic study of nosocomial infections in a pediatric long–term care facility," *Am. J. Infect. Control* 21:183–188 (Aug., 1993).

Voss, J.G., "Effects of Organic Cations on the Gram–negative Cell Wall and Their Bactericidal Activity with Ethylenediamine–tetra–acetate and Surface Active Agents," *J. gen. Microbiol.* 48:391–400 (Sep., 1967).

Wenzel, R.P., "Healthcare workers and the incidence of noscomial infection: can treatment of one influence the other?—A brief review," *J. Chemother.* 6:33–37 and 39–40 (Sep., 1994).

"Public Health Focus: Surveillance, Prevention, and Control of Nosocomial Infections," *Morbidity and Mortality Weekly Report* 41:783–787 (Oct., 1992).

"Guidelines for Management of Patients with Methicillin–Resistant *Staphylococcus aureus* in Acute Care Hospitals and Long–Term Care Facilities," *Connecticut Med.* 517:611–617 (Sep., 1993).

Dialog File 351, Derwent WPI, English language abstract for JP 56–25139 (Document AL1).

Dialog File 399, CA Search, description for CS 202494 (Document AM1).

Dialog File 351, Derwent WPI, English language abstract for JP 4–134025 (Document AN1).

Patent Abstracts of Japan, English language abstract for JP 5–39498, published Feb. 19, 1993.

Patent Abstracts of Japan, English language abstract for JP 5–105618, published Apr. 27, 1993.

Patent Abstracts of Japan, English language abstract for JP 5–229916, published Sep. 7, 1993.

Patent Abstracts of Japan, English language abstract for JP 7–267844, published Oct. 17, 1995.

Patent Abstracts of Japan, English language abstract for JP 9–25221, published Jan. 28, 1997.

Patent Abstracts of Japan, English language abstract for JP 9–157700, published Jun. 17, 1997.

Patent Abstracts of Japan, English language abstract for JP 9–235369, published Sep. 9, 1997.

LONG CHAIN CARBOXYBETAINES IN ANTIMICROBIAL FORMULATIONS

This appln is a 371 of PCT/US97/18256 filed Oct. 10, 1997, and also a continuation of Ser. No. 08/730,733 filed Oct. 11, 1996, abnd.

FIELD OF THE INVENTION

The present invention is related to the use of long chain carboxybetaines in antimicrobial formulations. These compositions are especially useful as disinfectants or antiseptic preparations against Staphylococcus, especially, *Staph. aureus*, and *Staph. epidermidis,* Salmonella, especially *Salmonella typhimurium,* Escherichia and Pseudomonas, especially *Ps. aeruginosa.*

BACKGROUND OF THE INVENTION

A. Nosocomial Infections

A nosocomial infection (NI) is defined as a disease acquired by a patient at a health care facility (i.e. not the patient's original disorder). Many NI are caused by microorganisms that can naturally colonize the external surfaces of the body (e.g. skin, moist mucosal surfaces or GI tract), however, under certain conditions these "opportunists" can cause disease. For example, NI are often associated with invasive medical procedures, such as surgery and bronchoscopy, and with penetrating devices, such as catheters. Furthermore, intensive care patients are particularly at risk of NI, especially in surgical, pediatric/neonatal, burns and trauma units (Martin, M.A. *New Horizons* 1:162–171, (1993)). The predominant causes of NI are gram positive bacteria (>40%), especially *Staphylococcus aureus* and *Staphylococcus epidermidis*, and gram negative bacteria (>40%), especially *Escherichia coli*, with the remaining NI being caused mainly by yeast and fungi (Vermaat et al. *American Journal of Infection Control* 21:183–188, (1993)). Gram positive bacteria, such as *Staph. aureus*, are of particular concern due to their hardiness (ability to survive under non-physiologic conditions) and their inherent resistance to many antibiotics. Each year, NI affect an approximately 2 million patients, cause more than 60,000 deaths and incur an estimated $4.5 billion in added costs (*Morbidity and Mortality Weekly Reports* 41:783–787, (1992); Pittet, D. & Wenzel, R. P. *Archives of Internal Medicine* 155:1177–1184, (1995)). These figures have been increasing progressively over the last 10 years.

A component of NI that is an increasing problem is the incidence of drug-resistant microorganisms. This problem is highlighted in a recent monologue by Stuart B. Levy, M.D. (Levy, S. B., *The Antibiotic Paradox. How Miracle Drugs are Destroying the Miracle.*, Plenum Press, New York (1992)), which describes a number of case studies involving outbreaks of multi-drug resistant (MDR) strains of bacteria. One example of this is the "golden staph" or methicillin-resistant *Staphylococcus aureus* (MRSA). The incidence of MRSA varies between health care facilities and countries, however, it can be greater than 50% of all *Staph. aureus* isolates, and appears to be increasing, especially in Japan (Lotsu et al. *Jour. Hosp. Infection,* 27:275–283, (1995)). Disease caused by MRSA can be effectively treated with vancomycin, however, there is concern that inappropriate use of this antibiotic may lead to the emergence of vancomycin-resistant MRSA. Disease caused by this organism will be extremely difficult to treat, tantamount to a death sentence.

The incidence of NI, including MRSA, can be reduced by at least 30% by implementing suitable infection control measures, however, in the US, only 6%–9% of NI are actually being prevented (Hospital Infections Program, Centers for Disease Control and Prevention). Of particular concern is the fact that a common reservoir for MRSA is the nasal passages of health care workers, with hand contamination often being the route of transfer (Guidelines for management of patients with methicillin-resistant *Staphylococcus aureus* in acute care hospitals and long-term care facilities. *Connecticut Medicine* 57:611–617 (1993); Wenzel, R. P. *Journal of Chemotherapy* 6 suppl. 4:33–40, (1994)). Consequently, a major component of successful infection control programs is an emphasis on hand washing and effective use of sterilizing procedures, disinfectants and antiseptics (CDC Guidelines for Handwashing and Hospital Environmental Control).

Gram-negative microorganisms, as exemplified by *Salmonella, Pseudomonas,* and virulent strains of *E. coli,* are also important bacteria both clinically and also to the food industry. *Salmonella* is a major cause of food poisoning—caused by the ingestion of meat (or items in contact with the meat) of diseased animals. *Pseudomonas* is widely distributed in water and air, on the skin and in the upper respiratory tract, and can be isolated from feces. It is clinically associated with other pyrogenic organisms in abdonimal acscesses, and can cause cystitis, otitis media, mastoiditis, enteritis in children and even septicemia.

As with gram positive microorganisms, such infections can be extremely difficult to treat. Prevention of such infections, especially clinically and in the food industry, is grounded on the effective use of sterilizing procedures, disinfectants and antiseptics. The effective use of reagents that could be used as disinfectants, or more importantly antiseptics, that could efficiently eliminate pathogenic microorganisms would help to alleviate the burden of medical costs attributable to such infections.

B. Disinfectants and Antiseptics

Germicidal activities are generally discussed in terms of sterilization, disinfectant properties and antiseptic qualities. Sterilization involves the use of chemical or physical means to totally eliminate microorganisms, viruses, fungi, spores, yeast and other saprophytic and infectious agents, independent of type or classification (e.g., autoclaving or irradiation).

Disinfectants are, by definition, germicidal agents used on inanimate objects. Disinfectants are typically chemical agents that are generally less broad in terms of their spectrum of activity, relative to sterilizing procedures. As a result, not all forms of a given category of organism are killed, but pathogenic forms are preferentially eliminated by design.

Antiseptics are, by definition, germicidal agents designed for use on living or biological tissue, primarily skin and hair. Antiseptics are typically milder chemical agents than disinfectants and, as a result, are generally less efficacious at eliminating infectious agents. For example, disinfectants usually incorporate organic reagents that would be unacceptable in antiseptic formulations due to toxicity, carcinogenic or mutagenic activity. Since routes of infection are typically through a breach in tissue, or via a natural opening, antiseptic formulations provide perhaps the most important line of defense.

Unfortunately, the dichotomy between toxicity and efficacy precludes many disinfectants from being used as antiseptics. Additionally, many microbial pathogens are resistant to commonly used disinfectants and antiseptics. There is a need for bactericidal compositions, especially disinfectant and antiseptic compositions, that are efficacious, and that are economical to make and use.

C. Detergents as Disinfectants and Antiseptics

In general, nonionic detergents have been reported to have minimal, if any, bactericidal activity, whereas ionic detergents, such as the quaternary amines, have been reported to have bactericidal activity (Cella, J. A. et al., *J Am. Chem. Soc.* 74:2061–2062 (1952)). Cella also reported that, in general, quaternary amine detergents that have longer alkyl chains also have greater bactericidal activity than their shorter chain counterparts.

However, ionic detergents are generally untenable as components in aqueous antiseptic and disinfectant formulations due to a lack of solubility in the presence of ions. If provided in the precipitated form, the reagent is less available and less efficacious. Nonionic detergents are, for the most part, unaffected by the presence of ions so, at a first glance, would appear to be suitable for antiseptic and disinfectant preparations. However, such detergents are not ideal for the purposes of decontamination, due to their relatively poor bactericidal activity.

A decrease in solubility in the presence of ions is called "salting-out." When ionic detergents are placed in the presence of ions (e.g., NaCl), there is a "Krafft point elevation" (e.g. the temperature required to maintain the detergent in solution is increased). In other words, the heat of mixing required to maintain the detergent molecules in solution is increased; below the Krafft point, the detergent precipitates (or "salts") out of solution.

As an example of salting-out, the temperature required to maintain $C_{12}$-sulfonate in solution in pure water is 31.5° (Tartar, H. V et al., Jour. Am. Chem. Soc. 61:539–544 (1939)), but 34° C. in 8 mM salt (Tartar, H. V. et al., Jour. Phys. Chem. 43:1173–1179 (1939)). Thus, the Krafft point elevation, or "salting-out effect," is 3.5° C. under these conditions. The salting-out behavior of $C_{14}$-sulfonate occurs at 39.5° C. and 43° C. in water and saline, respectively (Tartar, H. V et al., Jour. Am. Chem. Soc. 61:539–544 (1939), Tartar, H. V. et al., Jour. Phys. Chem. 43:1173–1179 (1939)). The Krafft temperature of $C_{18}$-sulfonate in pure water begins at 57° C. (Tartar, H. V et al., Jour. Am. Chem. Soc. 61:539–544 (1939)).

Betaines are zwitterionic detergents and are commonly found in commercial preparations of soaps, shampoos, laundry detergents, cosmetics and other toiletries. In addition to their use as surface active agents, it has been reported that certain of the n-alkyl betaines have bactericidal activity. Betaines have been used as antimicrobials in commercial formulations of antioxidants (Němcová, J., et al. CS 202494 B), cleansers (Gomi, T. JP 8895298 2; JP 6395198) and detrifice preparations (Oshino K., et al., JP 92134025 A2; JP 04134025).

Voss et al. *J. Gen. Microbiol.* 48:391–400 (1967) reported on the bactericidal activity of sulfopropylbetaines, and Tsubone et al. *J. Phar. Sci.* 80:441–444 (1991) studied the action of phosphatobetaines. Tsubone reported that both $C_{16}$-phosphatoethylbetaine and $C_{16}$-phosphatobutylbetaine have greater bactericidal activity than $C_{16}$-phosphatopropylbetaine. $C_{16}$-phosphatoethylbetaine had the highest degree of bactericidal activity of those Tsubone tested. Unfortunately, solubility can be a problem with the longer chains on these betaines.

Since the n-alkyl betaines have been used in both topical emollients and antimicrobial formulations, they appear to be attractive candidates for inclusion into disinfectant and antiseptic preparations. However, there are limitations, such as the salting out characteristic discussed above, and others as discussed further herein, that have prevented the widespread effective commercial use of n-alkyl betaines in antiseptic and disinfectant concoctions.

D. Betaine Chemistry

The most common n-alkyl betaines utilize natural oils as the alkyl chain (e.g., coconut oil), and the charges are usually separated by a methylene bridge. Cococarboxymethylbetaine is probably the most common commercially available betaine, and is a primary component of many shampoo formulations.

The betaine detergents, as a group, are extremely heterogeneous with respect to structure and composition. For example, there are n-alkyl betaines that incorporate phosphates (e.g., phosphatobetaines), phosphonates (e.g., phosphonobetaines), and phosphinates (e.g., phosphinobetaines), sulfates (e.g., sulfatobetaines), sulfonates (e.g., sulfobetaines), and oxide radicals (e.g., amine oxides) as the anion. The structure of the "bridge" (e.g., "$R_4$" (see Table 1)) separating the charges can include, in addition to methylene, ethylene, propylene, butylene, and longer hydrocarbon-like chains, aromatic or hydroxyl groups, or even a simple covalent bond, as in the case of amine oxides. Further, it is not uncommon to have aminopropyl or carbonyl functions "linking" (e.g., "α" (see Table 1)) the alkyl chain to the ammonium.

The physical properties of n-alkyl betaines are entirely dependent on structure. For example, changing the anion from a sulfate, to a sulfonate, to a carboxylate, to a phosphate, causes a change in character from that of a nonionic detergent to that of an ionic detergent. The sulfatobetaine is extremely nonionic in nature, whereas the sulfonate has both ionic and nonionic characteristics (Nilsson, P. et al., *J. Phys. Chem.* 88:6357–6362 (1984)). Alternatively, the carboxy- and phosphato-betaines are completely ionic in nature with the phosphatobetaine being the extreme ionic example (Tsubone, K. et al., *J. Am. Oil. Chem. Soc.* 67:394–399 (1990)). Betaines can also be swayed toward a nonionic or ionic character depending on other structural moieties on the molecule (e.g., the bridge ($R_4$; see Table 1) or the linkage (α)).

One unique aspect of betaine behavior that separates this class of detergents from both ionic and nonionic detergents is the fact some betaines can be "salted-in," as opposed to the ionic detergents, which are "salted-out." If a compound is salted-in, the detergent becomes more soluble (i.e., the Krafft temperature is reduced) in the presence of salt. Betaines that have been commonly used in commercial preparations have been of the salting out type; that is, they would not be soluble in the ionic conditions commonly found in antiseptic and disinfectant compositions.

Betaines with bridge lengths less than 4~5 Å typically salt-out in the presence of salt (e.g., similar to ionic detergents). Betaines using a methylene bridge (i.e., $R_4$ is —$CH_2$—) have a charge separation of approximately 3.1 Å(Tsujii, K. et al., *Yakagaku* 30:495–499 (1981)). The carboxymethylbetaines of Michaels (U.S. Pat. No. 4,062, 976, U.S. Pat. No. 4,075,350, U.S. Pat. No. 4,107,328, U.S. Pat. No. 4,145,436, U.S. Pat. No. 4,183,952, U.S. Pat. No. 4,839,158, U.S. Pat. No. 5,244,652 and U.S. Pat. No. 5,389,676) have a bridge length of less than 4~5 Å and thus would behave in a manner similar to anionic detergents and be of the salting-out type.

Salting-in behavior is extremely dependent on bridge length and structure. N-dodceyl amino-propionic acid possesses the carboxylate anion with an ethylene bridge (i.e., $R_4$ in Table 1 is —$C_2H_4$—). Tsujii, K. et al., *Yakagaku* 30:495–499 (1981) report that the distance separating the charges in N-dodecylamino-propionic acid is 4.5 Å, and that this detergent is of the salting-in type.

Thus, no one class of betaines has been reported to have the desired combination of bactericidal activity, aqueous solubility, and ease of manufacture that is necessary to facilitate the wide-spread economical commercial use of n-alkyl betaines in antiseptic and disinfectant concoctions.

SUMMARY OF THE INVENTION

Recognizing the current deficiencies in antiseptic and disinfectant formulations, and especially antiseptic formulations, and cognizant of the need for an inexpensive yet efficacious reagent capable of eliminating infectious agents from such formulations, the inventors examined the use of betaines to kill such infectious agents. The inventors have discovered that a certain class of betaines, n-alkyl carboxybetaines were surprisingly and unexpectedly efficient at eliminating both gram positive and gram negative microorganisms, and especially representative members of those classes that have historically been very difficult to kill.

The inventors' studies culminated in the formulation of a simple composition, containing one or more n-alkyl carboxybetaines, and preferably, CB-18. This composition is highly efficient at killing gram positive microorganisms, including *Staph. aureus* and gram negative microorganisms, including *Salmonella typhimurium, E. coli* and *Pseudomonas* in a reasonable period of time.

Thus, in a first embodiment, the present invention provides compositions containing one or more n-alkyl carboxybetaines, at concentrations effective in killing infectious agents, and especially microorganisms, and most especially gram positive microorganisms, especially *Staph aureus* and *Staph. epidermidis* and gram negative microorganisms, such as, for example, *Salmonella typhimurium, Pseudomonas* and *Escherichia*, such as, for example, *E. coli.*

In a further embodiment, the n-alkyl cabroxybetaines present in the composition comprise N-(3-carboxypropyl)-N,N-dimethyl-1-octadecanaminium, inner salt ($C_{18}$-carboxypropylbetaine (CB-18 (CAS® No. 78195-27-4))).

In a further embodiment, the compositions are formulated as a disinfectant composition.

In a further embodiment, the compositions are formulated as an antiseptic composition.

In a further embodiment, the compositions are formulated as a preservative composition for the long term storage of other solutions, or items in the solution, under conditions that minimize or prevent bacterial growth.

In a further embodiment, the present invention provides methods for the use of the above compositions for the eradication of any infectious agent, especially microorganisms, and most especially gram positive microorganisms, such as, for example, *Staph. aureus* and *Staph. epidermidis* and gram negative microorganisms, such as, for example, *Salmonella, Escherichia* and *Pseudomonas* in a reasonable period of time.

In a further embodiment, the invention provides a method for disinfecting an inanimate object.

In a further embodiment, the invention provides a method for antiseptically cleaning living or biological objects or matter, including tissue or organs.

DETAILED DESCRIPTION OF THE PREFERRED EMBODIMENTS

Figure 1:
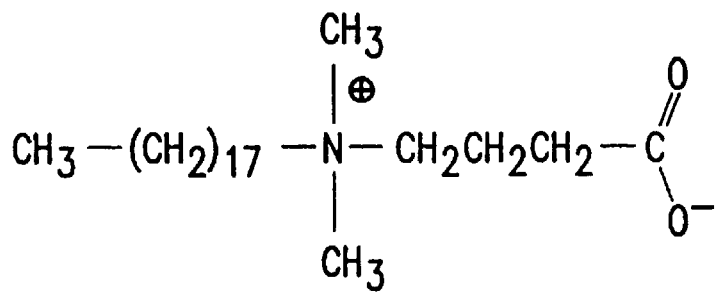
FIG. 1 shows the structure of N-(3-carboxypropyl)-N,N-dimethyl-1-octadecanaminium, inner salt, also known as $C_{18}$-carboxypropylbetaine, and referred to herein as CB-18. CB-18 has been assigned the CAS® No. 78195-274.

In the description that follows, a number of terms used in germidicial technology are extensively utilized. In order to provide a clear and consistent understanding of the specification and claims, including the scope to be given such terms, the following definitions are provided.

By "infectious agent" is meant a bacterium, a virus, a fungus, yeast or prion that, under the appropriate conditions can cause disease or otherwise be undesirably introduced into or present in a human or animal, as understood in the art (Isenberg, H. D. et al., In: *Manual of Clinical Microbiology* 6$^{th}$ Edition, Murray, P. R. et al., eds. ASM Press, Washington, D.C. (1995) pp5–18, incorporated herein by reference). These agents can either be infectious in nature (e.g., *Staphylococcus, Streptococcus*, Influenza, HIV, *Salmonella* or *Histoplasma* species), or indigenous organisms found in or on the human body (e.g., natural colonizers of skin or gut.) In the latter case these saprophytic agents (e.g., *Staph. epidermidis, Escherichia coli,* or *Bacillus* species, or *Pneumocystis* species) become infectious due to a breach or immunological incompetence of the host.

By "microorganism" is meant a prokaryotic organism as understood in the art (Joklik, W. K. et al., *Zinsser Microbiology* 20$^{th}$ Edition, Appelton & Lange, Norwalk, Conn., (1992) pp. 3–17), incorporated herein by reference). Prokaryotic organism is synonymous with microorganism.

By "gram positive microorganism" is meant a microorganism that is characterized in that it has a cell wall structure in which the peptidoglycan chains are cross-linked by peptide bridges (e.g., amino acids) as understood in the art (Joklik, W. K. et al., *Zinsser Microbiology* 20$^{th}$ Edition, Appelton & Lange, Norwalk, Conn., (1992) pp.76–93), incorporated herein by reference).

By "gram negative microorganism" is meant a microorganism with an outer structure composed of a cytoplasmic (inner) membrane separated from an outer membrane by a thin layer of peptidoglycan.

By "carboxybetaine" is meant an n-alkyl betaine of the structure shown in Table 1.

TABLE 1

The Structure of n-alkyl Carboxybetaines
The general structure of an n-alkyl caboxybetaine is shown.
By definition, the cation is an ammonium and the anion is a carboxylate.
$R_1$ is the alkyl chain, and α links the alkyl chain to the ammonium
(e.g., the "linkage"). $R_2$ and $R_3$ modify the ammonium to stabilize
the charge structure. $R_4$ is the "bridge" that separates
the ammonium from the carboxylate.

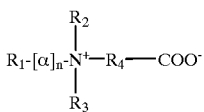

| | |
|---|---|
| $R_1$ | $C_{12}$—$C_{22}$ |
| α | —$CH_2$—, —CH(OH)—, —(CO)—NH—$CH_2CH_2CH_2$—, —O—, —(CO)— |
| n | 0 or 1 |
| $R_2$ | —H, —$CH_3$, —$C_2H_5$, —$C_3H_7$ |
| $R_3$ | —H, —$CH_3$, —$C_2H_5$, —$C_3H_7$ |
| $R_4$ | —$C_2H_4$—, —$C_3H_6$—, —$C_4H_8$—, —$C_5H_{10}$—, —$C_6H_{12}$—, —$CH_2$—$C_6H_4$—, —$C_mH_{2m}$—, —CH(OH)$CH_2CH_2$—, —$CH_2$CH(OH)$CH_2$—, —$CH_2CH_2$CH(OH)—, —$C_mH_{2m-1}$(OH)—, where m≥2 |

By "disinfectant" is meant a germicidial (bactericidal) composition that is used to kill microorganisms on inanimate objects such as sinks, toilets and bathroom fixtures, as well as counter tops, floors, and walls.

By "antiseptic" is meant a germicidial (bactericidal) composition that is used to kill microorganisms on living or biological objects or matter, including tissue or organs, such as skin and hair.

By "CB-18" is meant N-(3-carboxypropyl)-N,N-dimethyl-1-octadecanaminium, inner salt. CB-18 is also known as N,N-dimethyl-N-(n-octadecyl)-N-(3-carboxypropyl) ammonium inner salt, or $C_{18}$-carboxypropylbetaine. CB-18 has been assigned the CAS® No. 78195-27-4.

n-alkyl-Carboxybetaines

Table 1 shows the general structure of n-alkyl carboxybetaines. By definition, and as shown in Table 1, an n-alkyl carboxybetaines is an n-alkyl betaine that utilizes ammonium as the cation and a carboxylate as the anion. The composition and method of the invention utilize an n-alkyl carboxybetaine, preferably an n-alkyl carboxybetaine as shown in Table 1. Such n-alkyl carboxybetaines are characterized in having:

(1) a long chain alkyl ($R_1$ in Table 1) of 12–22 carbons;
(2) a bridge ($R_4$) as shown in Table 1 that is at least an ethylene bridge and is preferably a butylene bridge or most preferably a propylene bridge;
(3) substituents modifying the ammonium ($R_2$ and $R_3$) as shown in in Table 1, preferably methyl;
(4) a linkage, (α) as shown in Table 1, and preferably, a simple methylene linkage; and
(5) a carboxylate anion.

The n-alkyl carboxybetaines of the invention show salting-in behavior. This salting-in characteristic allows the n-alkyl carboxybetaines of the invention to remain in solution with the longer alkyl chains attached as described above. The distance separating the charges must be greater than 4~5 Å in order to exhibit salting-in behavior.

The ability of an n-alkyl carboxybetaine to salt in is also dependent on the charges employed. The more polarized the anion, the less dramatic the salting-in behavior. For example, the Krafft temperature of $C_{18}$-carboxypropylbetaine (CB-18) drops from 25° C. in pure water to approximately 19° C. in salt (Δ≈6° C.) (Tsujii, K. et al. Yakagaku 30:495–499 (1981)).

The bridge structure of the n-alkyl carboxybetaines of the invention can play a role not only in physical behavior, but also in bactericidal activity. The ethyl and butyl bridges are preferred as imparting a greater bactericidal activity to the overall structure than the propyl bridge.

The structures of $R_2$ and $R_3$ can also affect the bactericidal activity of the n-alkyl carboxybetaines. The bactericidal activity of the compound is likely to be diminished as these substituents increase from methylene, to ethylene to propylene. Steric hindrance may interfere with uptake of the reagent by the bacteria (Tsubone et al., *J. Phar. Sci.* 80:441–444 (1991)).

N-(3-carboxypropyl)-N,N-dimethyl-1-octadecanaminium, inner salt ($C_{18}$-carboxypropylbetaine (CB-18)) (CAS® No. 78195-27-4) is the highly preferred n-alkyl carboxybetaine of the invention. Neither the spectrum nor degree of the bactericidal activity of the salting-in n-alkyl carboxybetaines, especially CB-18, have been described, nor has a "salting-in" n-alkyl carboxybetaine, especially CB-18, been incorporated as a component in a disinfectant or an antiseptic preparation.

CB-18 utilizes a carboxylate anion (e.g., $COO^-$: ionic in nature), an octadecyl tail (e.g., a long chain) and a propylene bridge (e.g., a bridge of the salting-in type). N-alkyl carboxybetaines are easily manufactured using techniques known in the art. For example, CB-18 (i.e., $C_{18}$-carboxypropylbetaine) is a single step synthesis wherein the purification step is coincident with the formation of the final product (Kazuo J P 8125139). The method of Kazuo J P 8125139, or modifications thereof, have the advantage that they obviate the requirement for further purification, a significant commercial advantage. The method of Kazuo JP 8125139 can be modified to use ethyl 4-bromobuterate (CAS® No. 2969-81-5), a compound more readily available commercially. It would be reasonably expected that carboxybetaines possessing ethylene bridges could also be manufactured using the preferred method of Kazuo JP 8125139 by exchanging the ethyl 4-iodobuterate (or ethyl 4-bromobuterate) precursor with either ethyl 3-chloropropionate (CAS® No. 623-71-2) or ethyl 3-bromopropionate (CAS® No. 539-74-2). Carboxybetaines possessing propylene or ethylene bridges with varying chain lengths could be manufactured using these preferred synthetic methods (e.g., Kazuo JP 8125139) by simply using the appropriate n-alkyl dimethylamine precursor having the desired chain length. Techniques in the art indicate that the manufacture of n-alkyl carboxybetaines possessing bridges wherein $R_4$≥4 (e.g., butylene, pentylene, hexylene, bridges etc.) are more difficult and/or costly to manufacture than their ethylene or propylene counterparts due to the need for extensive purification. The manufacture of other betaines, such as, for example, phosphobetaines is, however, even more complex.

Alternatively to CB-18, preferred n-alkyl carboxybetaines useful in the compositions and methods of the invention include CB-12, CB-13, CB-14, CB-15, CB-16, CB-17, CB-19, CB-20, CB-21 or CB-22. The preferred carboxybetaines in the compositions and methods of the invention utilize either ethylene or propylene bridges ($R_4$), propylene being preferred. Such n-alkyl carboxybetaines can also contain alkyl chains of varying lengths, for example, $R_1$=12, 13, 14, 15, 16, 17, 18, 19, 20, 21 or 22 carbon atoms; it is especially preferred that $R_1$ contains 16–20 carbons, 18 carbon atoms being most preferred.

The inventors have discovered that n-alkyl carboxybetaines provide an ideal combination of salting-in behavior, economy of production and use, and possess a surprisingly high bactericidal activity against a wide range of bacteria.

The compositions of the invention are bactericidal against a wide variety of bacteria, including *Escherichia, Staphylococcus, Salmonella,* and *Pseudomonas*. Surprisingly, the compositions of the invention are especially bactericidal against species that can be difficult to kill, including *Staphylococcus aureus, Staphylococcus epidermidis, Salmonella typimiurium* and *Pseudomonas aeruginosa* and virulent strains of *E. coli*.

Hence, according to the methods of the invention, the viability, and thus the infectivity of infectious agents can be decreased or eliminated by causing the n-alkyl carboxybetaine-containing composition of the invention, preferably in solution, to come in contact with the infectious agent for such a time, and under such conditions, that the viability, or infectivity, of said agents are compromised.

In a first preferred embodiment, a disinfectant composition is provided that contains one or more n-alkyl carboxybetaines, and preferably, one or more salting-in n-alkyl carboxybetaines, most preferably at least CB-18, in an amount that is efficacious at providing bactericidal activity when applied to an inanimate object. Such composition is preferably formulated as a solution in which the n-alkyl carboxybetaine(s) is dissolved, most preferably an aqueous solution, and less preferably as a precipitate or power. If formulated as a precipitate or power it is prefeable that such precipitate or powder is capable of dissolving into an aqueous solution when mixed with such, for example, at a desired site. The disinfectant composition is delivered onto the surface being disinfected in any form that retains the efficacious properties of the disinfectant, for example, a liquid, cream or aerosolized spray. The n-alkyl carboxybetaine solution is left in contact with the surface being disinfected for such a time as to permit killing of the infectious agent(s).

In a second preferred embodiment, an antiseptic composition is provided that contains one or more n-alkyl carboxybetaines, and preferably, one or more salting-in carboxybetaines, and most preferably at least CB-18, in an amount that is efficacious at providing bactericidal activity when applied to living or organic objects, matter, tissue or organs and the like, without harm to the object, matter, tissue or organ or the like. The antiseptic composition is provided in any form that retains the antiseptic property of the composition, preferably as a solution in which the n-alkyl carboxybetaine(s) is dissolved, most preferably an aqueous solution, or as a power or precipitate. If formulated as a precipitate or power it is prefeable that such precipitate or powder is capable of dissolving in an aqueous solution, for example at the site being treated. The antiseptic composition is conveninetly applied to the site being made aseptic as a liquid, an aerosolized spray, or as a cream, and is left in contact with that site for such a time as to permit killing of infectious agent(s).

The concentrations of the long chain carboxybetaine, and especially of CB-18, in the disinfectant and antiseptic compositions and methods of the invention can be any concentration that will impart the desired bactericidal effect. Preferably the concentration ranges from about 10 $\mu$M to about 10 mM. The concentration useful in a specific embodiment is limited on the lower side by the critical micellar concentration and on the higher side by the solubility of the n-alkyl carboxybetaine compound. For example, the critical micellar concentration of CB-18 is 40 $\mu$M. In a preferred embodiment, the concentration of the n-alkyl-carboxybetaine, and especially CB-18, is greater than 40 $\mu$M in the final composition. CB-18 is not very soluble at concentrations greater than about 10 mM. However, for use in the invention, no significant advantage is seen at concentrations greater than about 2 mM. Accordingly, in a first embodiment, the concentration of n-alkyl carboxybetaine, and especially CB-18, is 40 $\mu$M to 10 mM. In an especially preferred embodiment, the concentration is 100 $\mu$M–4 mM. In a highly preferred embodiment, the concentration is 1 mM–2 mM, although clearly other concentrations, such as 3 mM, 5 mM, 7 mM and 8 mM can be used. The compositions of the invention be prepared in the form of a "concentrate" that is intended to be diluted by the user.

The compositions of the invention are effective within minutes of contact. Exposure to a 1 mM concentration of an n-alkyl carboxybetaine of the invention for even seconds, and especially for 1, 5, 10, 15, 20 or 30 minutes will provide bactericidal effects, with increasing effect being seen for the longer times. For example, 1 mM CB-18 reduced the numbers of viable *Staphylococcus aureus* and *Salmonella typhimurium* by about 99% within 15 minutes. Compared to a solution of 1% household bleach (an intermediate-level disinfectant), and 2-chloro-3,5-dimethylphenol (CdMP; a.k.a. chloroxylenol or parachlorometaxylenol; a common component in bactericidal soaps and a preservative in cosmetics), 1 mM CB-18 had an equivalent bactericidal activity (i.e. the ability to kill bacteria) as that of 1% bleach and was, surprisingly, over 50,000-times more active against *Staph. aureus* and, also surprisingly, over 40-times more active against *Salmonella* than 1 mM CdMP. Thus, in a high preferred embodiment, the bactericidal activity of the compositions of the invention is directed against microorganisms, and most especially gram positive microorganisms, especially *Staph. aureus* and *Staph. epidermidis,* or gram negative microorganisms, especially *Salmonella* and especially *Salmonella typhimurium,* and *Escherichia* and especially *E. coli,* or *Pseudomonas,* and especially *Ps. aeruginosa.*

The n-alkyl-carboxybetaines compositions of the invention may be provided in any physical form, including a powder, solution, emulsion, suspension, extract, collodion, elixir, or lotion as desired to impart the bactericidal effect, alone or in combination with other ingredients that impart a desired effect to the solution, including perfuming agents. The composition of the invention, especially in dried or gel form, or as a liquid contained within an enclosure such as, for example, a capsule, from which it is capable of diffusing or being released, can be provided as part of a physical structure, such as a bandage or microparticle, such that the bactericidal composition is provided to the desired site (for example, the wound that the bandage covers) at efficacious amounts for prolonged periods of time.

The bactericidal compositions of the invention are intended to be applied topically to an inanimate object or living or biological objects or matter, including tissue or organs, although, if desired, the compositions can be perfused into the biological objects or matter, including tissue or organs. The antiseptic compositions may be utilized on any biological objects or matter, including tissue or organs in need of the antiseptic properties that can be provided by the n-alkyl-carboxybetaine-containing compositions of the invention, including human, animal or plant tissue.

The bactericidal antiseptic compositions of the invention are especially useful in the processing of food products that are intended for human or animal consumption, for example, meat (and especially animal carcasses), vegetables and fruits. The compositions of the invention can be applied to the food product in any convenient manner, for example, by spray or wash or by dipping the product into the composition. The bactericidal compositions of the invention are allowed to remain in contact with the food product for the desired time to achieve an efficacious bactericidal effect, for example, 1, 5, 15 min or 30 min, and then the composition of the invention is preferably rinsed off the food product. Such treatment is especially useful in the processing of beef (cattle), pork (pigs), mutton (sheep, lamb), poultry (chicken and turkey) and seafood for human and animal consumption. The food product can be treated more than once if desired. For example, the food product can be treated by the food processing plant, and again, if desired, by the consumer prior to consumption.

Alternatively, the bactericidal antiseptic compositions of the invention, are useful as an aseptic lavage of organs intended for transplantation, or as an antiseptic solution in which to wash or soak wounds prior to dressing.

Compositions containing one or more n-alkyl carboxybetaines, especially one or more salting-in n-alkyl carboxybetaines, and most especially CB-18, can also be formulated, preferably as dilute solutions specifically as mouthwashes, or gargles to provide efficacious amounts of the bactericidal n-alkyl carboxybetaine to the oral cavity including the pharynx and nasopharynx. Swallowing should be avoided.

Compositions containing n-alkyl carboxybetaines, and especially salting-in n-alkyl carboxybetaines, and most especially CB-18, may also be formulated specifically as a cleaning/disinfecting composition, or preservative to prevent the growth of microorganisms in a solution, alone or in combination with other agents. Such cleaning, preservative or disinfectant compositions are useful, for example, for the cleaning, storing and disinfecting of contact lenses.

The compositions of the invention are preferably homogeneous mixtures that are in solution. Additional agents may be provided, including additional bactericidal agents, including antibiotics, as long as such agents do not detract from the bactericidal activity of the n-alkyl carboxybetaine (s) present in the composition. For example, the combination of CB-18 and CdMP (both at 1 mM) abrogated the activity of CB-18. Agents that enhance or facilitate the bactericidal effect of the n-alkyl carboxybetaine(s) are preferable. For example, the composition of the antiseptic can include buffers (for example, Tris), chelating agents, (for example, EDTA), or other agents (such as mild organic or aromatic compounds, for example, low amounts of ethanol or isopropanol) that work in concert or synergistically with the n-alkyl carboxybetaine(s) or combinations of such agents, that facilitate the bactericidal effect, or otherwise impart a desired property to the composition.

The invention is described in more detail in the following examples. Example 1 exemplifies the processing of clinical specimens with an n-alkyl carboxybetaine, CB-18. Example 2 exemplifies the bactericidal activity of the n-alkyl carboxybetaines, in particular, CB-18, against *Staphylococcus aureus* in a nutrient medium. Example 3 exemplifies the bactericidal activity of a representative n-alkyl carboxybetaine, CB-18, against *Staphylococcus aureus* in a buffered medium. Examples 4–5 demonstrate the bactericidal activity of a representative n-alkyl carboxybetaine, CB-18, against the gram-positive bacteria, and especially *Staphylococcus aureus*, and against gram-negative bacteria, especially *Salmonella typhimurium*. Example 5 demonstrates the bactericidal activity of a representative n-alkyl carboxybetaine, CB-18, against *E. coli* and *Pseudomonas aeruginosa*. These examples show only a few concrete applications of the invention. It is self evident for one skilled in the art to create several similar applications. Hence the examples should not be interpreted to narrow the scope of the invention only to clarify the use of the invention.

EXAMPLES

Example 1

Processing Clinical Specimens with CB-18

Thornton, C. G. (WO 95/27076) recently described the use of betaine for the preparation of Mycobacteria from clinical specimens. That method was designed to replace the current methods of processing clinical specimens (Kent, P. T. et al., "Public Health Mycobacteriology" in *A Guide for the Level III Laboratory*, U.S. Department of Health and Human Services, Centers for Disease Control (1985), 31–46). During the development of that procedure, the inventors recognized the integral nature of processing specimens by a particular technique, for culture using a specific method. For example, in the United States, clinical specimens are typically decontaminated using the NALC/NaOH procedure (Kubica, G. P. W. et al., *Am. Rev. Resp. Dis.* 87:775–779 (1963)) and the resulting sediments inoculated into BACTEC 12B culture bottles supplemented with the antibiotic cocktail PANTA (a combination of Polymixin B, Azlocillin, Naldixic acid, Trimethoprim, and Amphotericin B). The sodium hydroxide treatment kills many of the saprophytic and infectious organisms associated with the specimen. Many of the surviving organisms are further selected against by incorporation of the antibiotic supplement. It is important to recognize that the antibiotic supplement was optimized for use in conjunction with the NALC/NaOH treatment (Siddiqi, S. H. et al., Abstract U-35, A.S.M. Annual Meeting, Washington, D.C. (1986)). Due to the fact that betaines have known bactericidal activity, it would be reasonably expected that switching from NALC/NaOH processing to betaine processing would cause a dynamic change in the flora surviving the decontamination method and, therefore, breaking through in the culture system (e.g., BACTEC 12B/PANTA). Studies were undertaken to understand this dynamic change.

Two hundred and seventy seven (277) discarded respiratory specimens were processed using a modified version of the betaine methods described by Thornton (WO 95/27076) as follows: Approximately 2 mls of specimen was placed in a 50 ml conical tube. An equal volume of 0.5% NALC/1.45 mM sodium citrate was added and the mixture incubated at room temperature for 10 minutes. The volume was then brought to approximately 36 mls with sterile, filtered water. Four mls of a 10× buffered CB-18 solution was added to the mixture (the final concentration (e.g., 1×) of the buffer components was as follows: 50 mM Tris-HCl pH 8.0, 1 mM NaCl, 1 mM CB-18 and 5 mM NALC). Each specimen was mixed and then incubated at 37° C. for 90 minutes with shaking. Following the incubation period the tubes were subjected to centrifugation at 4,000×g for 20 minutes at 30° C. The tubes were then decanted and 500 µl of sterile, filtered water added to resuspend the pellet. A volume of 400 µl was then added to a BACTEC 12B culture bottle (Becton Dickinson, Cockeysville, Md.) supplemented with PANTA (Becton-Dickinson, Cockeysville, Md.) according to the manufacturer's instructions. The bottles were checked periodically for growth. A small volume of media from positive cultures was transferred to a blood plate (Becton Dickinson, Cockeysville, Md.) to check for contamination. Growth on the blood plate indicated breakthrough contamination in the BACTEC 12B/PANTA culture system. Individual colonies were picked for analysis by gram staining (Chapin, K. In: *Manual of Clinical Microbiology* 6th Edition, Murray, P. R. et al., eds. ASM Press, Washington, D.C. (1995) pp39–41). Gram positive organisms were then examined for oxidase activity using Oxidase Reagent Droppers (Becton Dickinson, Cockeysville, Md.), and gram negative organisms checked for catalase activity using standard procedures (Ruoff, K. L. In: *Manual of Clinical Microbiology* 6th Edition, Murray, P. R. et al., eds. ASM Press, Washington, D.C. (1995) pp.318). Final identification and sensitivity profiles were defined using MicroScan® panels (Dade International, Sacramento, Calif.).

A subset of the 277 specimens above were also processed by the standard sodium hydroxide decontamination method (Kubica, G. P. W, et al., *Am. Rev. Resir. Dis.* 87:775–779 (1963)) using the BBL® MycoPrep™ kit (Becton Dickinson, Cockeysville, Md.). Specimens were processed according to the instructions of the manufacturer. Briefly, specimens were split such that 2 mls were processed using CB-18 as described above, and 2 mls of the same specimen were incubated with an equal volume (e.g., 2 mls) of a solution containing 2% sodium hydroxide (NaOH), 0.5% N-acetyl-L-cystiene (NALC) and 1.45 mM sodium citrate (referred to herein as NALC/NaOH). The NALC/NaOH procedure required that the specimens be incubated at room temperature for 20 minutes. Following the incubation period the specimens were neutralized with the buffer provided (K·Na—PO$_4$pH6.8) by bringing the final volume to 50 mls with this buffer. The specimens were then subjected to centrifugation at 4,000×g for 20 minutes at 4° C. Cultures were prepared, processed and contaminants identified as described above.

Table 2 shows the overall results of all 277 specimens (e.g., CB-18 data only). Table 3 shows the subset of 133 specimens processed by both NALC/NaOH and CB-18. Table 2 shows that the population of organisms breaking through CB-18 processed respiratory specimens, cultured in the BACTEC 12B/PANTA system, are dominated by gram negative rods (84.2%) Approximately 62% of these gram negative rods were enterobacteriaceae. Less than 9% of the contaminants were seen to be gram positive, only 5.3% were yeast contaminants, and 1.8% fungal contaminants.

TABLE 2

Breakthrough Contaminants from CB-18 Processed Specimens (n = 277)

| Group | # | % (of total) | Group | # | % (of total) |
|---|---|---|---|---|---|
| Gram Negative | 48 | 84.2% | Enterobacteriaceae | 30 | 62% |
|  |  |  | Other Gram Neg Rods | 18 | 38% |
| Gram-Positive | 5 | 8.8% |  |  |  |
| Yeast | 3 | 5.3% |  |  |  |
| Fungal | 1 | 1.8% |  |  |  |
| Total | 57 | From 40 Specimens = 14.4% Contamination Rate |  |  |  |

When specimens were split such that they were processed by both CB-18 and the NALC/NaOH protocol of Kubica, G. P. W. et al., *Am. Rev. Resp. Dis.* 87:775–779 (1963) the NALC/NaOH protocol showed 107 contaminants, with 67.0% being gram negative and 28.5% being gram positive (Table 1B). The same set of specimens processed by CB-18 showed only 32 breakthrough contaminants: almost 88% were gram negative, and only 6% were gram positive in origin. Only 13 of the gram negative isolates were common between NALC/NaOH and CB-18, neither of the gram positive CB-18 isolates were coincident with NALC/NaOH, and only 1 of the fungal contaminants overlapped. This indicated that CB-18 had an unexpectedly high activity against *Staph. aureus* and other gram positive organisms.

TABLE 3

Breakthrough Contaminants: CB-18 vs. NALC/NaOH Processed Specimens (n = 133)

| Group | CB-18 | NALC/NaOH |
|---|---|---|
| Gram Negative | 28 (87.5%) | 72 (67.3%) |
| Gram Positive | 2 (6.2%) | 30 (28.0%) |
| Yeast | 2 (6.2%) | 4 (3.7%) |
| Fungi | 0 | 1 (0.9%) |
| Total | 32 Isolates | 107 Isolates |
| From: | 21 Specimens | 74 Specimens |
| Contamination Rate: | 15.8% | 55.6% |

The results seen in Table 3 are generally unexpected for two reasons. First, the fact that CB-18 provides a greater decontamination capacity than 2% NaOH (1% final concentration) is surprising. Second, the contamination rate is much higher than most laboratories experience (e.g., for those practicing NALC/NaOH). In actuality, while 2% NaOH (1% final) is recommended (Kent, P. T. et al., "Public Health Mycobacteriology" in *A Guide for the Level III Laboratory*, U.S. Department of Health and Human Services, Centers for Disease Control (1985), p.31–46), most clinical laboratories use a much higher concentration of NaOH (i.e., up to 4% (2% final concentration)). An additional feature of this data that may affect these results stems from the origin of the specimens: they were culled from the specimens submitted to the microbiology laboratory for routine analysis. Consequently, they may not accurately reflect the population of specimens submitted to the TB-laboratory for AFB analysis. The important aspect of Table 3, however, is the fact that there is a dynamic change in the flora surviving decontamination when CB-18 is used, and that there is a dramatic bias against gram positive organisms when CB-18 is used.

Example 2

Bactericidal Activity of CB18 against *Staphylococcus aureus* in a Nutrient Medium (tryptic soy broth)

In the Example 1, respiratory specimens processed with CB-18 showed a lower incidence of contamination than respiratory specimens processed by the traditional NALC/NaOH protocol. Furthermore, the decontaminating effect of CB-18 was most apparent against gram positive microorganisms. Thus studies were undertaken to investigate this phenomenon further, specifically to analyze the bactericidal activity of CB-18 against the clinically important gram positive bacterium, *Staphylococcus aureus*.

Typically, the bactericidal (bacterial killing) activity of an agent is assessed in one of two ways: either by determining the minimum bactericidal concentration (MBC); or by a time-kill assay (Knapp, C. et al., In Clinical Microbiology Procedures Handbook vol. 1, American Society for Microbiology, Washington, D.C. (1992) pages 5.16.1–5.16.33). Both approaches analyse the number of viable organisms remaining in a nutrient broth culture after a period of incubation in the presence of the test agent. The MBC approach uses as an end point the concentration of test agent that kills 99.9% of the added bacteria after a 20 h incubation. Time-kill assays (or kill curves) monitor the numbers of viable organisms over time and thus provide kinetic analysis of the activity of an agent. For time-kill assays, a 99.9% decrease in viability is considered an adequate bactericidal response. Since time-kill assays provide more information on the activity of a test compound, this approach was adopted for the analysis of the bactericidal activity of CB-18.

The procedure used for the time-kill assay of CB-18 against *Staph. aureus* strain ATCC 29213 was modified from Knapp and Moody as follows. A 50 mL suspension of *Staph. aureus*, with a turbidity of Macfarland 0.5, was prepared in tryptic soy broth. This suspension was dispensed in 5 mL aliquots into 6 sterile culture tubes to which was added either: (a) 50 µL, (b) 100 µL or (c) 250 µL of 100 mM CB-18 (final CB-18 concentrations were 1, 2 and 4 mM, respectively); (d) 250 µL of 50% isopropanol in double distilled water ($ddH_2O$); (e) 50 µL of household bleach; or (f) 250 µL of $ddH_2O$ (control). The tubes were vortexed and then incubated at room temperature. One hundred µL aliquots were removed from each tube at times 0, 15, 30 and 60 min. of incubation and each immediately diluted in 10-fold steps to a final level of 1/10,000. For the 1/100, 1/1,000 and 1/10,000 dilutions, 100 µL aliquots were spread on separate tryptic soy agar plates, which were then incubated overnight at 37° C. From the colony forming units (CFU) counted on the agar plates, the viable CFU/mL of each culture was determined. Using these values, the percentage viable organisms was calculated with reference to the control culture (f) time 0 CFU/mL.

Figure 2:
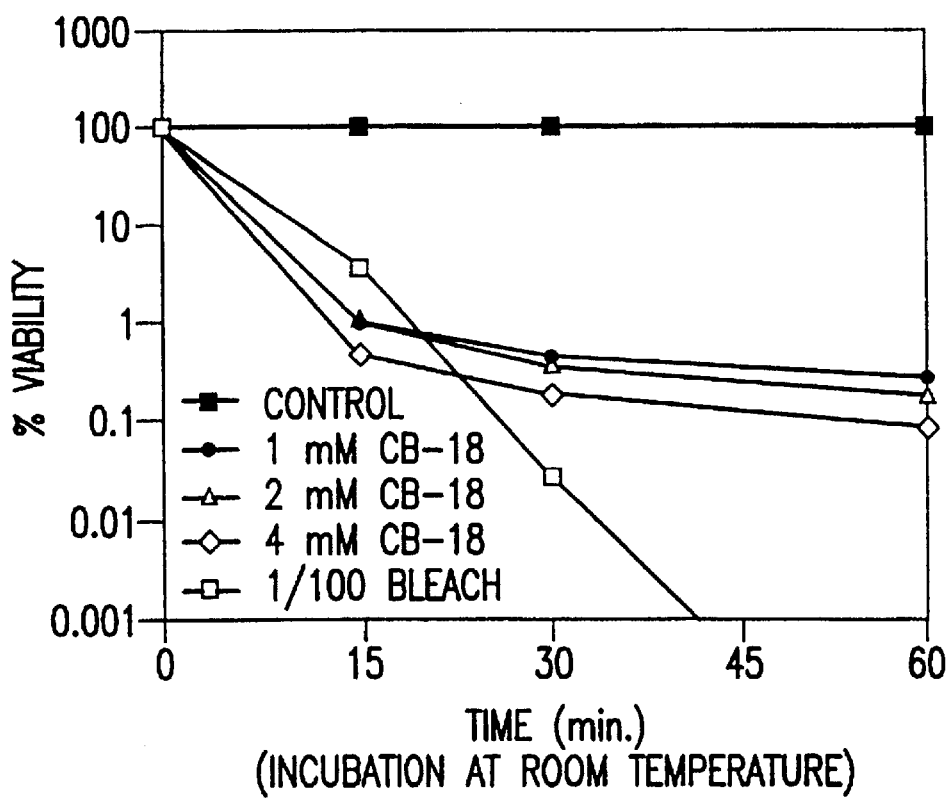
FIG. 2 shows the effect of CB-18 on the survival of *Staph. aureus* ATCC 29213 in a nutrient medium. Filled squares: control; filled circles: 1 mM CB-18; open triangles: 2 mM CB-18; open diamonds: 4 mM CB-18; open squares: 1/100 dilution of bleach. Incubation was at room temperature for the indicated period of time.

FIG. 2 shows the percent viable organisms for each culture condition against time. The isopropanol culture (d) showed no significant killing and was not plotted. All three concentrations of CB-18 tested killed at least 99% of Staph. aureus within 15 min, which was more than the 96% killed by a 1/100 dilution of bleach (which is considered an intermediate level disinfectant). However, after this time, the bactericidal activity CB-18 decreased; CB-18 at 4 mM required 60 min. to achieve 99.9% killing. The time for the 1/100 dilution of bleach to achieve 99.9% kill was 26 min.

Example 3

Bactericidal Activity of CB-18 against *Staphylococcus aureus* in a TE Buffer (pH 8.3)

In Example 2, the rapid (<15 min) bactericidal activity of CB-18 was demonstrated. However, the decrease in the activity after 15 minutes exposure suggests that CB-18 was unstable in the assay system. For example, CB-18 may have lost potency due to chemical degradation, chelation or precipitation. Alternatively, the bacteria may have become refractory to the effects of CB-18. Therefore, modifications were made to the system in an attempt to improve the observed bactericidal activity of CB-18.

The component of the assay which is most amenable to experimental manipulation is the aqueous medium. In Example 2, the medium was a complex nutrient broth, thus favoring the growth of the bacteria. Therefore, studies were undertaken to assess the bactericidal activity of CB-18 in non-nutrient solution. Previously, reagents such as ethylenediaminetetra-acetic acid (EDTA) and Tris (a combination of: 2-amino-2-(hydroxymethyl)-1,3-propanediol (Tris base) and 2-amino-2-(hydroxymethyl)-1,3-propanediol hydrochloride (Tris HCl)) were shown to affect the permeability of the cell wall of bacteria, especially gram negative bacteria (see discussions in: Hancock, R. E. W. *Ann. Rev. Microbiol.* 38:237–264 (1984), and Nikaido, H. et al., *Microbiol Rev.* 49:1–32 (1985)), making them more susceptible to lytic agents, without themselves being bactericidal (Voss, J. G. *J. Gen. Microbiol.* 48:391–400, 1967). Thus, a buffered aqueous solution of EDTA (TE buffer: 10 mM Tris-Cl, pH 8.3; 1 mM EDTA) was chosen as the assay medium.

The protocol was modified from Example 2 as follows. A suspension of *Staph. aureus* (from an overnight culture) was prepared in TE buffer and adjusted to a turbidity of Macfarland 0.5. This suspension was dispensed in 5 mL aliquots as in example 2, to which the test agents were added. The final concentrations of CB-18 used were 0.01, 0.1 and 1 mM. The negative control suspension had no additions and the reference disinfectant was a 1/100 dilution of Tergisyl™ (National Laboratories, Montvale, N.J.). Tergisyl™ is a cocktail of sodium xylene sulfonate, triethanolamine dodecylbenzene sulfonate, o-phenylphenol, trisodium ethylene diamine tetraacetate and p-tert-amylphenol. Viability of the *Staph. aureus* was assessed (as per example 2) after 5, 15, 30 and 60 min. after addition of the test agents.

Figure 3:
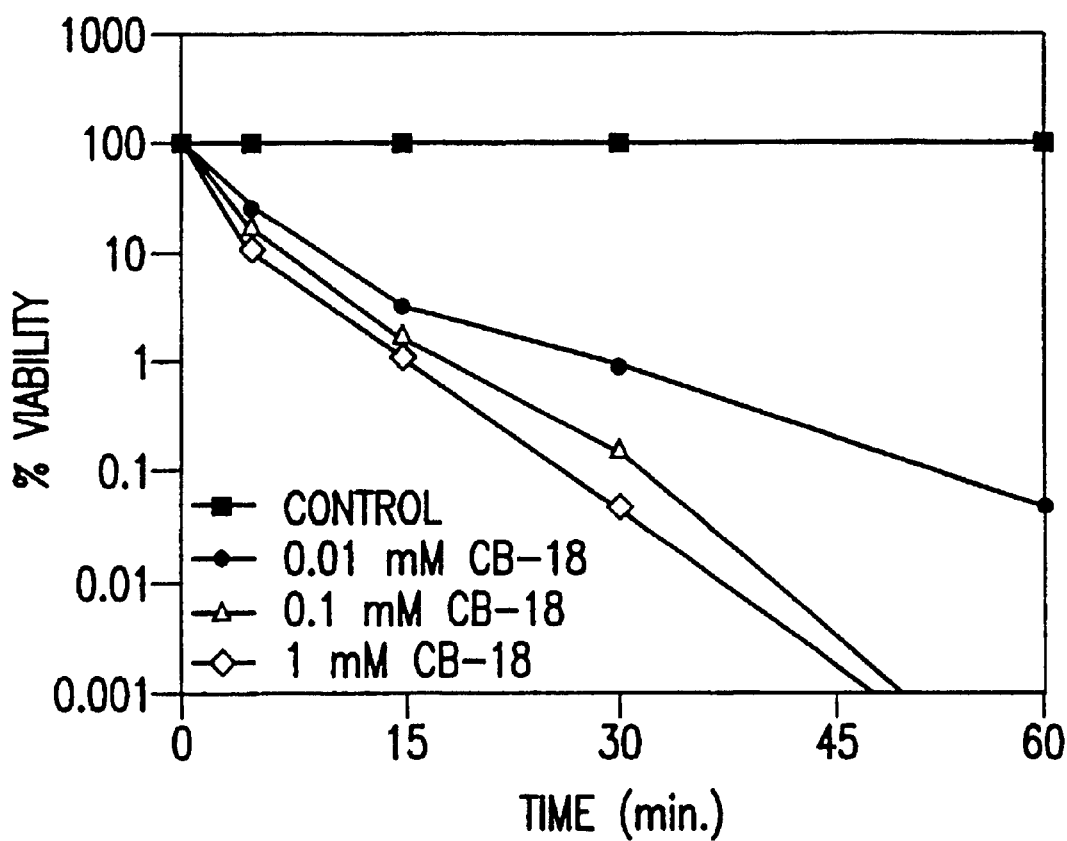
FIG. 3 shows the effect of CB-18 on the survival of *Staph. aureus* ATCC 29213 in TE buffer (10 mM Tris-HCl pH 8.0, 1 mM EDTA). Filled squares: control; filled circles: 0.01 mM CB-18; open triangles: 0.1 mM CB-18; open diamonds: 1 mM CB-18.

No viable *Staph. aureus* was detected at any time point after addition of Tergisyl™. FIG. 3 and Table 4 show the survival of *Staph. aureus* in 0.01–1 mM CB-18. After 5 min, 1 mM CB-18 had killed 90% of the original inoculum of *Staph. aureus*. After 15 min, 99% had been killed. This is comparable to the kinetics seen in example 2. Extrapolating from the data in FIG. 3, the times to reach 99.9% killing for 0.01, 0.1 and 1 mM CB-18 were 55, 32 and 27 min, respectively. Thus, by comparison with the results of example 2, the diluent can facilitate the bactericidal activity of CB- 18.

TABLE 4

Time required to reach 99.9% killing of $10^8$ CFU/ml *Staph. aureus*. Results were extrapolated from time-kill data.

| CB-18 Concentration (mM) | 99.9% kill time (minutes) |
| --- | --- |
| 1 | 27 |
| 0.1 | 32 |
| 0.01 | 54 |
| 1% Bleach | 30 |

Table 4 shows that CB-18 at either 0.1 or 1 mM reduced viable bacterial numbers by 99.9% or more within approximately 30 minutes. This was equivalent to the bactericidal activity of 1% bleach.

Figure 4:
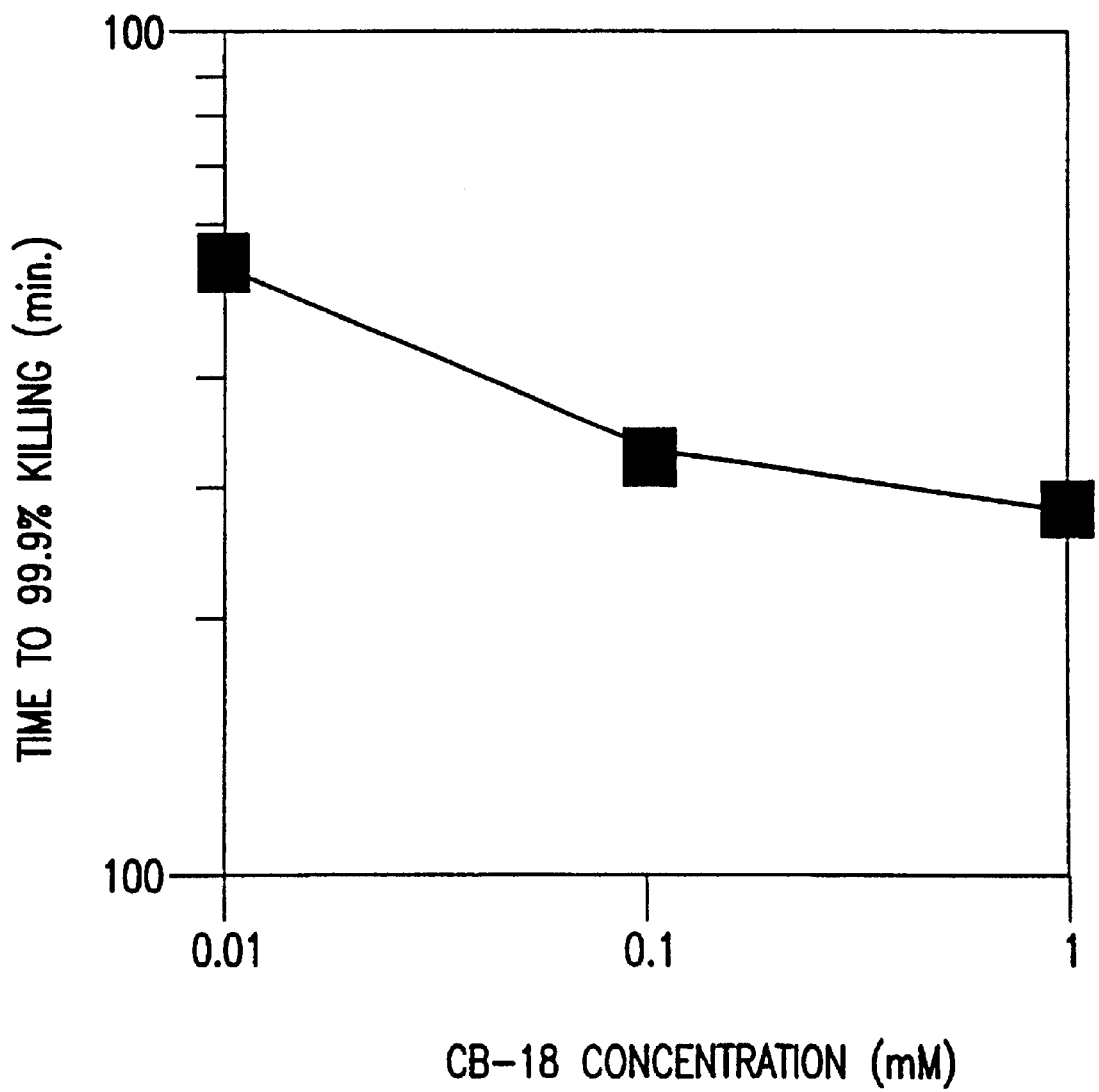
FIG. 4 shows the relationship between CB-18 concentration and bactericidal activity defined as the time required to reduce the numbers of viable organisms by 99.9%. Axes are logarithmic.

Over the concentrations tested, there appeared to be a logarithmic relationship between CB-18 concentration and bactericidal activity (FIG. 4). Despite this, increasing the concentration of CB-18 above 1 mM will probably only have a marginal effect on bactericidal activity against *Staph. aureus*. Higher concentrations may be beneficial in broadening than range of organisms that are killed by CB-18.

In summary, FIGS. 2 and 3 show that concentrations CB-18 from 0.01 to 1 mM are rapidly bactericidal to *Staph. aureus*, reducing the number of viable bacteria by >95 within 15 minutes. At each time point, 0.01 mM CB-18 was consistently less bactericidal than either 0.1 or 1 mM. Previous experiments had determined that the solvent used to initially dissolve the CB-18 (isopropanol) was not bactericidal at the maximum concentration (0.5%) in these experiments. CB-18 at concentrations of greater than or equal to 0.1 mM in TE buffer shows rapid (approximately 30 min.) bactericidal activity (>99.9% kill) against the gram positive organism, Staph. aureus. Whereas Tergisyl™ proved to be superior to CB-18, the following point should be recognized: Tergisyl™ is a complex mixture of surface active and organic reagents that has been optimized for non-antiseptic use. The composition of Tergisyl™ would preclude its use as an antiseptic.

Example 4

Bactericidal Activity of CB-18 against the Gram-Negative Bacterium, *Salmonella typhimurium*

Rationale

Having determined that CB-18 is active against the gram-positive bacterium, *Stph. aureus*, its activity against gram-negative bacteria needed to be assessed. *Salmonella typhimurium* was chosen as a model gram-negative bacterium because *Salmonella* species are important bacteria both clinically and also to the food production industry. The design of these experiments was similar to that in Example 3, except that it was expected that gram-negative organisms would be more resistant to CB-18 than gram-positive organisms (from the results in Example 1). Therefore the CB-18 concentration used was the same or higher than that in Example 3. In addition, a simpler approach was used: the bactericidal activity of different concentrations of CB-18 within a set time period (30 minutes) was determined, rather than assessing time-kill kinetics (Example 3).

2-Chloro-3,5-dimethylphenol (CdMP; a.k.a. chloroxylenol or parachlorometaxylenol) is a bactericidal agent found in many antibacterial soaps, usually at a concentration of about 0.5% (32 mM). This substance has also been used as a preservative in cosmetics (see Pat. Nos. 5,403,864 & 5,439,681). Since CB-18 has potential application to such products, CdMP was chosen as a comparator.

Results and Discussion

TABLE 5

Bactericidal activity of CB-18 and CdMP against *Staph. aureus*, and *S. typhimurium*

| Experimental Condition | Staph. aureus | | S. typhimurium | |
|---|---|---|---|---|
| (final concentration) | CFU/ml | % survival | CFU/ml | % survival |
| Time 0 | $7.60 \times 10^7$ | n/a | $8.60 \times 10^7$ | n/a |
| TE buffer control | $6.96 \times 10^7$ | 100.0 | $7.34 \times 10^7$ | 100.0 |
| Isopropanol (2.5%)† | $6.43 \times 10^7$ | 92.4 | $2.93 \times 10^7$ | 39.9 |
| CB-18 (10 mM) | $0^\Psi$ | $0.0^\Psi$ | $0^\Psi$ | $0.0^\Psi$ |
| CB-18 (1 mM) | $0^\Psi$ | $0.0^\Psi$ | $4.70 \times 10^4$ | 0.06 |
| CdMP (1 mM) | $5.46 \times 10^7$ | 78.5 | $1.90 \times 10^6$ | 2.6 |

†Concentration of isopropanol in 10 mM CB-18
$^\Psi$No CFU seen, however, limit of sensitivity was $1 \times 10^3$ CFU (0.001%)

As in Example 4, CB-18 at 1 mM reduced the viable *Staph. aureus* numbers by greater than 99.9% within 30 minutes. It was not possible to compare the relative bactericidal activities of 10 mM and 1 mM against *Staph. aureus*, since the detection limit of the assay was exceeded. However, previous experiments had shown only a marginally higher bactericidal activity of 10 mM compared with 1 mM.

CB-18 was less active against *S. typhimurium* than *Staph. aureus*; even so 1 mM did reduce viable bacterial numbers by >99.9%. However, unlike *Staph. aureus*, *Salmonella typhimurium* was significantly affected by 2.5% isopropanol (the concentration present in 10 mM CB-18). Taking this into account, both 10 mM and 1 mM CB-18 still caused a >99.9% reduction in CFU. For example, if the concentration of isopropanol in 1 mM was 2.5%, then CB-18 would have accounted for 99.8% drop in CFU/ml, i.e., the difference between $4.7 \times 10^4$ CFU/ml (1 mM CB-18) and $2.98 \times 10^7$ CFU/ml (2.5% isopropanol). In contrast, the concentration of isopropanol in 1 mM CB-18 was 10-fold lower, i.e. 0.25%.

The phenolic compound, CdMP, showed some bactericidal activity at 1 mM against *S. typhimurium* (97.4% reduction in CFU), however, it was relatively inactive against *Staph. aureus*. Higher concentrations of CdMP were not used because of the difficulty in maintaining this substance in aqueous solutions at concentrations above 1 mM. Despite this, on a molar basis, CB-18 was more than 50,000-times more active against *Staph. aureus* ($5.46 \times 10^7 / 1 \times 10^3$, from Table 5) and over 40-times more active against *S. typhimurium* ($1.90 \times 10^6 / 4.70 \times 10^4$, from Table 5) than CdMP.

Example 5

Bactericidal Activity of a Combination of CB18 and CdMP

Rationale

The use of combinations of antimicrobial agents is a relatively common practice in the treatment of infectious diseases. The benefits of combination are two-fold: they can be more effective than the individual agents alone; and they can reduce the probability of the emergence of drug-resistant organisms. Similar principles can apply to antiseptic and disinfecting formulations. Combinations of agents can have one of three effects on the overall antibacterial activity. Agents can be synergistic, that is the combined activity is greater than expected from activities of the agents alone. Agents can be additive, in that the combined activity equals the sum of the activities of the agents alone. Finally, agents can be antagonistic, that is the combined activity is less than expected from the activities of the individual agents. Evaluating how each component interacts in combinations will facilitate the development of improved formulations of active agents.

The basic experimental design was similar to that in Example 4, in that the bactericidal activity was assessed for set concentrations of CB-18 and CdMP after 30 minutes exposure. In these experiments *S. typhimurium* was used as the test organism since the activities of both CB-18 and CdMP at 1 mM were within the measurable range of the experimental system. Consequently, the bactericidal activity of combinations of the two agents should also be within the measurable range and hence allow the distinction of synergy, addition or antagonism.

Results and Discussion

TABLE 6

The bactericidal activity of a combination of CB-18 and CdMP (both at 1 mM) compared to the activity of the agents alone against *S. typhimurium*.

| Experimental Condition (final concentration) | CFU/ml | % Survival |
|---|---|---|
| Time 0 | $7.50 \times 10^7$ | n/a |
| TE buffer control | $7.10 \times 10^7$ | 100 |
| CB-18 (1 mM) | $3.13 \times 10^4$ | 0.04 |

TABLE 6-continued

The bactericidal activity of a combination of CB-18 and CdMP (both at 1 mM) compared to the activity of the agents alone against *S. typhimurium*.

| Experimental Condition (final concentration) | CFU/ml | % Survival |
|---|---|---|
| CdMP (1 mM) | $9.40 \times 10^6$ | 13.2 |
| CB-18 + CdMP(1 mM) | $1.15 \times 10^7$ | 15.3 |

Table 6 shows that a combination of CB-18 and CdMP, both at 1 mM was approximately as active as CdMP alone. Therefore, the two components acted antagonistically in combination, with, apparently, CdMP completely abrogating the activity of CB-18. These results are in contrast to the results of Example 3 wherein incorporation of a chelator (e.g., EDTA) into the disinfectant formulation enhanced the bactericidal efficacy of CB-18.

In summary, the results in Examples 4–6 show that CB-18 was bactericidal against a gram-positive bacterium (*Staphylococcus aureus*) and a gram-negative bacterium (*Salmonella typhimurium*). CB-18 was able to reduce viable bacterial numbers by >99.9% within 30 minutes exposure. This was equivalent to the bactericidal activity of 1% bleach, an intermediate-level disinfectant. CB-18 showed much greater bactericidal activity than CdMP, on a molar basis. Whereas combinations of EDTA and CB-18 were synergistic, combinations with CdMP completely abrogated the activity of CB-18.

Example 6

Bactericidal Activity of CB-18 against *E. coli* and *Pseudomonas aeruginosa*

The bactericidal activity of $C_{18}$-carboxypropylbetaine (CB-18) was assessed against the gram negative bacteria, *Escherichia coli* and *Pseudomonas aeruginosa*; both these organisms are a cause of morbidity and mortality in humans and animals. Many *E. coli* strains are not normally pathogenic to humans, however, there are strains (e.g., O157:H7) that can cause serious, often life-threatening, disease. Furthermore, *E. coli* is a major cause of bacteremia, sepsis, urinary tract infection, and nosocomial pneumonia. *Pseudomonas aeruginosa* is ubiquitous in the environment, and is considered an opportunistic pathogen, usually only causing disease in patients that are immunocompromised or with tissue damage. However, *Ps. aeruginosa* is intrinsically resistant to many disinfectants, antiseptics and a wide variety of antimicrobial agents. Consequently, persistent colonization with *Ps. aeruginosa* within the hospital environment is a major concern in the prevention of nosocomial infections.

The basic design of these experiments was the same as that in Example 4. Briefly, the two bacterial species were incubated in the presence of 1 mM CB-18 in TE buffer for 30 minutes, when the viable numbers of bacteria were assessed by determining CFU numbers. Since it was expected that CB-18 would be more active against *E. coli*, the numbers of viable organisms was also assessed after 10 minutes.

Results and Discussion

TABLE 7

Bactericidal activity against *E. coli* and *Ps. aeruginosa* of a 30 minute exposure to 1 mM CB-1

| Experimental Conditions (final concentration | *E. coli* | | *Ps. aeruginosa* | |
|---|---|---|---|---|
| | CFU/ml | % survival | CFU/ml | % survival |
| TE buffer control | $9.4 \times 10^1$ | 100.0 | $2.62 \times 10^5$ | 100.0 |
| CB-18 (1 mM) | $6.6 \times 10^2$ | 0.001 | 0* | 0* |

*No CFU seen, however, limit of sensitivity was 100 CFU (0.04% survival).

Table 7 shows that CB-18 at a concentration of 1 mM reduced the numbers of viable organisms by greater than 99.9% within 30 minutes of both of these bacterial species. The 99.9%-kill time for *E. coli* was 15 minutes, and for *Ps. aeruginosa* was estimated to be within 25 minutes. However, no definitive bactericidal activity of CB-18 against *Ps. aeruginosa* could be determined (no viable organisms detected after 30 minutes), therefore the 99.9%-kill time for this organism may be considerably less than 25 minutes.

Figure 5:
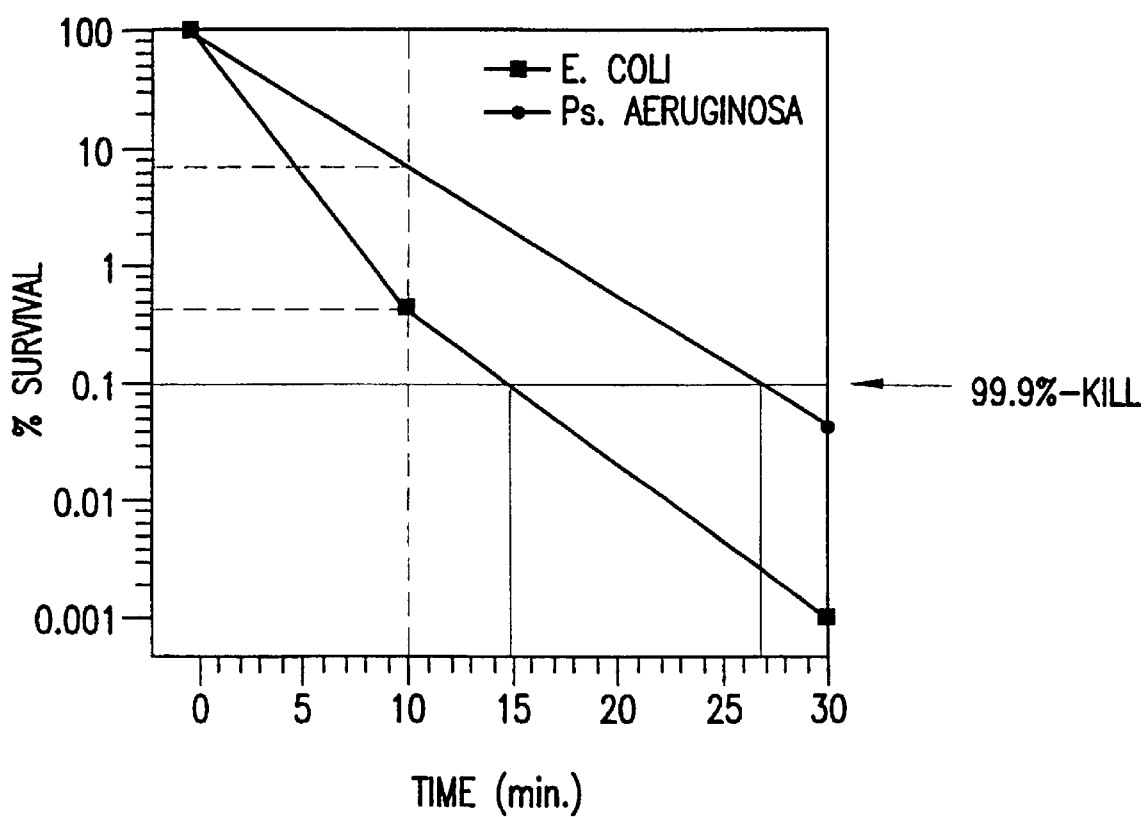
FIG. 5 shows the estimated time kill curves for 1 mM CB-18 against *E. coli* and *Ps. aeruginosa*. The *Ps. aeruginosa* data were based on the assay sensitivity, i.e., 0.04% survival. Solid squares: *E. coli*; solid circles: *Ps. aeruginosa*.

From FIG. 5, the 99.9%-kill time can be estimated; which for *E. coli* was approximately 15 minutes and for *Ps. aeruginosa* was approximately 26 minutes. However, the *Ps. aeruginosa* value may be significantly over-estimated since no definitive bactericidal activity was obtained for this organism; only that after 30 minutes less than 0.04% of bacteria remained. CB-18 maybe considerably more active against *Ps. aeruginosa* than these data suggest. The high activity against *Ps. aeruginosa* was especially surprising, because of the well-known intrinsic resistance of this organism to other disinfecting agents and antiseptics.

Having now fully described the invention, it will be understood by those with skill in the art that the invention may be performed within a wide and equivalent range of conditions, parameters and the like, without affecting the spirit or scope of the invention or any embodiment thereof. All references cited herein are fully incorporated herein by reference.

What is claimed is:

1. A method for killing an infectious agent, wherein said method comprises exposing said agent to a composition comprising a salting-in n-alkyl carboxybetaine, wherein said carboxybetaine is present in said composition at a concentration effective in killing said agent.

2. The method of claim 1, wherein said agent is a microorganism.

3. The method of claim 2, wherein said microorganism is a gram positive microorganism.

4. The method of claim 3, wherein said microorganism is a *Staphylococcus*.

5. The method of claim 4, wherein said *Staphylococcus* is *Staph. aureus*.

6. The method of claim 4, wherein said *Staphylococcus* is *Staph. epidermidis*.

7. The method of claim 2, wherein said microorganism is a gram negative microorganism.

8. The method of claim 7, wherein said microorganism is a *Salmonella, Pseudomonas* or *Escherichia*.

9. The method of claim 8, wherein said microorganism is an *Escherichia*.

10. The method of claim 9, wherein said *Escherichia* is *E. coli*.

11. The method of claim 8, wherein said microorganism is a *Pseudomonas*.

12. The method of claim 11, wherein said *Pseudomonas* is *Pseudomonas aeruginosa*.

13. The method of claim 8, wherein said microorganism is a *Salmonella*.

14. The method of claim 13, wherein said *Salmonella* is *Salmonella typhimurium*.

15. The method of any one of claims 1–14, wherein said n-alkyl carboxybetaine has the structure:

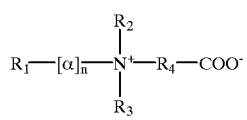

wherein $R_1$ is $C_{12}$ to $C_{22}$;

α is $-CH_2-$, $-CH(OH)-$, $-(CO)-NH-CH_2CH_2CH_2-$, $-O-$, or $-(CO)-$;

n is 0 or 1;

$R_2$ is $-H$, $-CH_3$, $-C_2H_5$, or $-C_3H_7$;

$R_3$ is $-H$, $-CH_3$, $-C_2H_5$, or $-C_3H_7$;

$R_4$ is $-C_2H_4-$, $-C_3H_6-$, $-C_4H_8-$, $-C_5H_{10}-$, $-C_6H_{12}-$, $-CH_2-C_6H_4-$, $-C_mH_{2m}-$, $-CH(OH)CH_2CH_2-$, $-CH_2CH(OH)CH_2-$, $-CH_2CH_2CH(OH)-$, or $-C_mH_{2m-1}(OH)-$, where $m \geq 2$; and the cation is a carboxylate.

16. The method of claim 15, wherein said n-alkyl carboxybetaine is CB-18.

17. The method of claim 15, wherein the concentration of said n-alkyl carboxybetaine in said composition is 10 μM–10 mM.

18. The method of claim 17, wherein said concentration is 40 μM–2 mM.

19. The method of any one of claims 1–18, wherein said composition is a disinfectant.

20. The method of any one of claims 1–18, wherein said composition is an antiseptic.

21. The method of any one of claims 1–18, wherein said composition is a preservative.

22. A method for decreasing the number of infectious agents on the surface of an inanimate object, said method comprising contacting said surface with a composition comprising a salting-in n-alkyl carboxybetaine, wherein said carboxybetaine is present in said composition at a concentration effective in decreasing the number of said infectious agents on said surface.

23. A method for decreasing the number of infectious agents on a living tissue, said method comprising contacting said tissue with a composition comprising a salting-in n-alkyl carboxybetaine, wherein said carboxybetaine is present in said composition at a concentration effective in decreasing the number of said infectious agents on said tissue.

* * * * *